(12) United States Patent
Jenkins et al.

(10) Patent No.: US 8,047,048 B2
(45) Date of Patent: Nov. 1, 2011

(54) TEST DEVICE FOR REFRACTORY MATERIAL

(75) Inventors: Robert J. Jenkins, Seabrook, TX (US); Donavin Duhon, League City, TX (US)

(73) Assignee: Robert J. Jenkins & Company, Webster, TX (US)

(*) Notice: Subject to any disclaimer, the term of this patent is extended or adjusted under 35 U.S.C. 154(b) by 56 days.

(21) Appl. No.: 12/697,084

(22) Filed: Jan. 29, 2010

(65) Prior Publication Data
US 2010/0192664 A1    Aug. 5, 2010

Related U.S. Application Data

(60) Provisional application No. 61/149,620, filed on Feb. 3, 2009.

(51) Int. Cl.
*G01N 3/56* (2006.01)
(52) U.S. Cl. ............................................................. 73/7
(58) Field of Classification Search .................... 73/7
See application file for complete search history.

(56) References Cited

U.S. PATENT DOCUMENTS

| | | | | | |
|---|---|---|---|---|---|
| 2,037,939 | A | * | 4/1936 | Spring et al. | 73/9 |
| 3,018,663 | A | * | 1/1962 | Dunlop | 374/7 |
| 3,221,534 | A | * | 12/1965 | Alfred et al. | 73/7 |
| 3,555,877 | A | | 1/1971 | Thelin | |
| 3,709,026 | A | | 1/1973 | Rhodes et al. | |
| 4,276,767 | A | * | 7/1981 | Cartwright | 73/7 |
| 4,986,109 | A | * | 1/1991 | Moon | 73/7 |
| 7,757,542 | B1 | * | 7/2010 | Jenkins et al. | 73/7 |
| 2008/0003125 | A1 | * | 1/2008 | Peterson et al. | 419/8 |

FOREIGN PATENT DOCUMENTS

JP    6-102160    4/1994

* cited by examiner

*Primary Examiner* — Hezron E Williams
*Assistant Examiner* — Mark A Shabman
(74) *Attorney, Agent, or Firm* — Buskop Law Group, PC; Wendy Buskop

(57) ABSTRACT

A system for testing abrasion resistance of a test specimen made of refractory material, wherein the system includes an insulated furnace with a first chamber having a refractory lining, a second chamber disposed within the first chamber, a tube for flowing pressurized air into the second chamber, a conduit for flowing heated air from a burner operating on a fuel to the second chamber, for mixing with the pressurized air, and an air gun for mixing an abrading material into the pressurized air prior to introduction to the test specimen.

19 Claims, 4 Drawing Sheets

US 8,047,048 B2

TEST DEVICE FOR REFRACTORY MATERIAL

CROSS REFERENCE TO RELATED APPLICATIONS

This application claims priority and the benefit of U.S. Provisional Patent Application Ser. No. 61/149,620 filed on Feb. 3, 2009, entitled "Test Device for Refractory Material," which is hereby incorporated in its entirety.

FIELD

The present embodiments generally relate a system for testing abrasion resistance of a test specimen.

BACKGROUND

A need exists for a system for testing abrasion resistance of a test specimen by preheating a test specimen without preheating the abrasive material prior to introducing the abrasive material to the heated test specimen to qualify material of test specimens and compare test specimen properties.

The present embodiments meet this need.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present system in detail, it is to be understood that the system is not limited to the particular embodiments and that it can be practiced or carried out in various ways.

The present embodiments relate a system for testing abrasion resistance of a test specimen.

The embodiments can further relate a system, which includes an insulated furnace with a first chamber having a refractory lining, a second chamber disposed within the first chamber, a tube for flowing pressurized air into the second chamber, a conduit for flowing heated air from a burner operating on a fuel to the second chamber, for mixing with the pressurized air, and an air gun for mixing an abrading material into the pressurized air prior to introduction to the test specimen.

The benefit to this test is to be able to perform blast type abrasion test at elevated temperatures. This test will allow for the comparison of different material's abrasive resistance at a given temperature. This will allow for the materials to be compared in side by side tests. This test method will also enable for a database to be generated for the properties of different materials. This data base will allow different batches of materials to be compared to a standard generated by knowledge gained from this test. This test will also allow for the elevated temperature erosion resistance of different abrading media to be compared.

Figure 1:
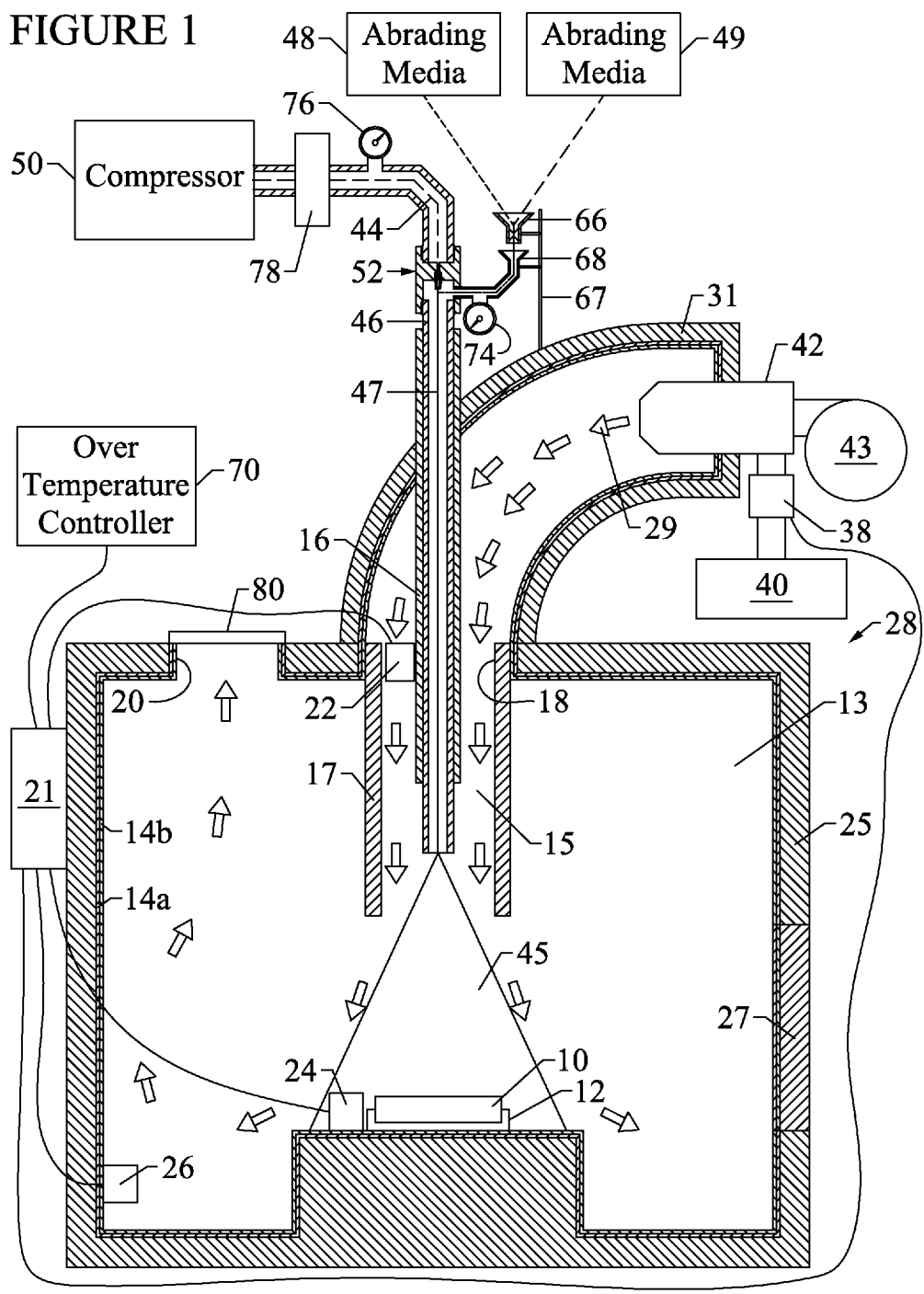
FIG. 1 depicts a schematic of the system with the insulated furnace.

Turning now to the Figures, FIG. 1 shows the system for testing abrasion resistance of a test specimen 10 at elevated temperatures hereinafter referred to as test temperatures from about 230 degrees Fahrenheit to about 2000 degrees Fahrenheit.

The test specimen can be a material capable of resisting deformation at elevated temperatures. The test specimen can be a refractory material, a metal, a ceramic, a ceramic and metal, a composite of ceramic and glass, a composite of ceramic and another material or combinations of these.

The test specimen can be a substrate, which can further have a coating disposed on the substrate, and the coating can be a material capable of resisting deformation at an elevated temperature. If the test specimen is a coating, the coating can be a ceramic and metal coating or another composite such as ceramic and metal. The coating can be from about ¼ inch to about 1/100 inch in thickness.

The test can be initiated by determining a density of at least one test specimen and a weight of the at least one test specimen The test can be concluded by calculating a volume of lost material from the test specimen that occurred during a specified test duration. The test uses an abrading media striking the test specimen at a defined angle, such as at about 10 degrees to about 90 degrees, at a defined temperature, such as from about 230 degrees Fahrenheit to about 2300 degrees Fahrenheit for a specific duration of time such as from about 7 minutes to about 2 hours, and possibly longer for certain types of material or if multiple types of abrading material need to be impacted on the test specimen.

These calculations can be made after the test specimen is removed from the furnace and weighed to determine weight loss using a known density thereby determining a volume of loss of the test specimen.

The Figure depicts an insulated furnace 28 that can be a 3 foot by 3 foot housing 25 or the housing can have another dimension. An example of this type of furnaces can be made by Robert J. Jenkins and Company of Houston, Tex. The insulated furnace 28 can sustain temperatures from about 100 degrees Fahrenheit to about 3000 degrees Fahrenheit.

In housing 25 of the insulated furnace 28 can be a first chamber 13. The first chamber 13 can be lined with at least one refractory material 14a, however the first chamber can also be lined with two different refractory materials 14a, and 14b, shown in this Figure, which can be layered on top of each other or positioned adjacent each other depending on the properties needed in the insulated furnace.

Examples of refractory material can be a ceramic or an insulating material capable of a low thermal conductivity from about 3 k to about 10 k.

The lining of the first chamber can be a single lining of one refractory material, or two layers forming one lining, where the first layer can be a first material and the second layer can be a second material, which can provide two different properties to the insulated furnace 28 increasing the versatility of the furnace. The lining can be from about 2 inches to about 8 inches in thickness.

From the top of the insulated furnace 28 and into the first chamber can extend inner wall 17 which can form a second chamber 15 within the first chamber 13, which is also shown in this Figure. The inner wall 17 can be from about 0.5 inches to about 2 inches thick and can be made of dense, erosion resistant material, such as refractory material, composite material or a metal. The inner wall can be round, or formed in the shape of an angular octagon, hex, or a box.

Within the inner wall 17 can be a tube 46 that can extend from the top of the insulated furnace 28 to the second chamber 15. The tube 46 can be from about 8 inches to about 24 inches long and can be connected to the top of the furnace using welds. The inner diameter of the tube 46 can be from about 1/8th inches to about 1 inch. The tube can be tapered and be shaped from wider to narrower towards the test specimen.

The tube 46 can be made of steel, stainless steel or another material that resists deformation under the temperatures of the insulated furnace 28. The tube 46 can extend from inside the insulated furnace 28 and can project beyond the top of the insulated furnace 28 up to several inches.

The inner wall 17 can be a single continuous wall in an embodiment, in a shape that is other than round having an open end facing a test specimen 10 that is on a substrate, such as a carrier 12 inside the first chamber 13.

The carrier 12 can be a plurality of plates connected together or supported in a set of parallel rails, which can enable multiple test specimens to be tested sequentially.

Through the top of the insulated furnace 28 and providing an exit from the first chamber can be an exhaust port 20 for allowing air to exit the insulated furnace 28. The exhaust port can have a diameter from about 3 square inches to about 50 square inches.

The exhaust port can be flush with the top of the furnace and can be closable, such as with a valve, flap or similar device.

Through the top of the insulated furnace 28 can be a first air intake 16 which can allow air to enter the second chamber 15 through the tube 46 that is within the inner wall 17. The air of the first air intake 16 can be maintained at a temperature below the test temperature.

The first air intake 16 can have a diameter greater than tube 46 and a diameter less than the second air intake 18.

The air of the first air intake 16 can be at a temperature near ambient temperature, the second air intake 18 can be at a temperature above the test temperature and above the first air intake 16, and the exhaust port 20 can be at a temperature between the first and second temperatures.

The second air intake 18 can be through the top of the insulated furnace 28 and can connect to the second chamber 15 or integrally connected with the inner wall 17. The inner wall 17 and the second air intake 18 can be a single piece.

The air can enter the first chamber 13 through the second chamber 15 surrounding the tube 46. The air entering through the second air intake 18 can be maintained at a temperature above the test temperature which is defined herein to be from about 230 degrees Fahrenheit to about 2000 degrees Fahrenheit. The diameter of the second air intake 18 can range from about 3 inches to about 10 inches.

Connected to the insulated furnace 28, shown in FIG. 1 as installed on a side of the insulated furnace 28 opposite the first chamber, can be a controller 21. The controller 21 can have a processor, data storage connected to the processor and computer instructions in the data storage, which will be described later. The controller 21 can monitor temperature signals from the first and second and even third thermocouples and compare those signals with a predetermined limit in data storage and can further control the valve 38 that can restrict flow of a fuel 40 into the burner 42 that heat the air forming the heated air 29. The fuel 40 can be natural gas, propane or a similar gaseous fuel without solid or liquid constituents.

The controller 21 can be connected through the walls of the insulated furnace with a wired connection, a wireless connection, or jointly in a wired and wireless manner to at least three thermocouples, shown here as thermocouple 22, which is shown, adjacent the second air intake 18, second thermocouple 24 adjacent the test specimen, and third thermocouple 26 within the first chamber. The thermocouples can be those such as the k thermocouple made by L and L Furnace. The thermocouples can be used for monitoring air temperatures.

The controller 21 can be connected through the walls of the insulated furnace 28 or by a wireless connection, or jointly in a wired and wireless manner to a second thermocouple 24 for monitoring temperatures at the test specimen.

The insulated furnace 28 further has a closable opening 27, such as a door with a latch, for allowing at least one test specimen. Multiple test specimens to be placed in the insulated furnace for simultaneous treatment and faster results using less energy.

FIG. 1 also shows a burner 42 connected to a fuel 40, which can further be a fuel source, via a valve 38 such as a ball valve that can control the flow of a fuel to the burner 42. The burner can heat air forming heated air 29. The burner can be a burner such as the ones made by Eclipse of Rockford, Ill.

The burner 42 can be connected to a blower 43, which can supply ambient air to the burner 42. The burner can flow the heated air 29 through a conduit 31 to the second air intake 18 at a rate of flow from about 3 cubic feet per minute to about 45 cubic feet per minute.

The conduit 31 can be used for flowing heated air from a burner operating on a fuel to the second chamber, for mixing with the pressurized air, and an air gun for mixing an abrading media into the pressurized air prior to introduction to the test specimen. In additional embodiments, multiple conduits can be used.

An air compressor 50 such as those made by Sullivan, can be in fluid communication with a unique and specially crafted air gun 52, through a regulator 78, for introducing pressurized air 44 to an air gun 52. The air gun 52 can blend the pressurized air 44 with at least one abrading media 48 or 49. FIG. 1 shows two abrading medias being used in the system. The tube 46 can then carry the blended air 47 from the air gun down the tube, through the top of the insulated furnace 28 inside the inner wall 17 and out the tube inside the inner wall forming mixed air 45 above the test specimen 10, wherein the mixed air is essentially blended air 47 mixed with the heated air 29 from the burner 42.

Figure 3:
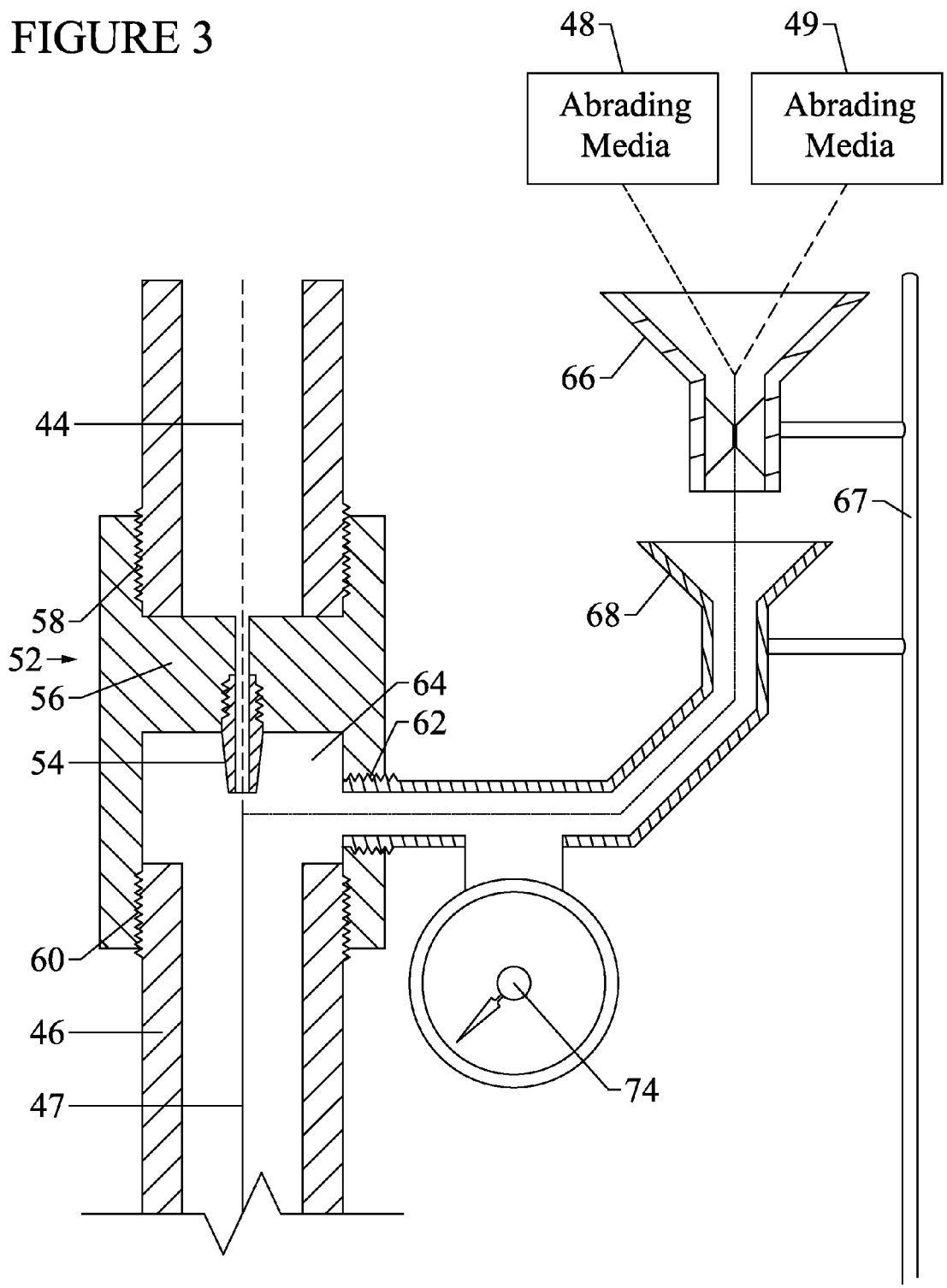
FIG. 3 is a cross sectional view of the air gun with meter and funnel used in the system.

Additionally, at least one abrading media source 48 and an additional abrading media source 19 can be connected to the air gun 52 for flowing abrading media into the pressurized air for introduction to the insulated furnace for impacting the test specimen 10, which can be seen in more detail in FIG. 3.

The abrading media can be introduced through a meter 66 connected to a pole 67. The pole 67 can hold the meter in alignment with a separated funnel 68 in this embodiment. The abrading media can flow from the separated funnel to the air gun 52.

The abrading media can be a flowable particulate, with particulate diameters from about $1/8^{th}$ inches to about 20 microns. The abrading media can be a silicon carbide grit, a catalyst, particulate of refractory material, or combinations thereof.

A unique feature of this test, is that it can be a one pass test method, providing very specific sized particulate diameters.

In another embodiment the funnel can be connected to the meter 66 which can be fluidly connected to the abrading media.

The meter can be a fixed orifice or a valve meter, such as one made by Robert R. Jenkins and Company of Houston, Tex. The pole can be made of metal, such as stainless steel and have a diameter from about ¼ inches to about 1 inches and can further be secured to a stand or foot for stability.

The meter and funnel can be disposed above the abrading media intake port of the air gun to create the negative pressure needed prior to entering the chamber of the air gun 52. The air gun 52 can be a T-shaped connection.

FIG. 1 also depicts a pressurized air gauge 76, which can monitor pressure of pressurized air 44 from the air compressor 50. A regulator 78 can be disposed in line from the air compressor 50 to the air gun 52 for controlling flow of pressurized air 44.

A negative pressure gauge 74 can be located between the separated funnel 68 and the air gun 52 and can monitor negative pressure of abrading media entering the air gun, which can also be shown in more detail in FIG. 3.

An over temperature controller 70 can be connected to the controller 21 and can provide emergency shut off of the insulated furnace 28 when temperatures in the furnace exceed a predetermined limit.

An exhaust valve 80 can be disposed over the exhaust port 20 for regulating exhaust air from the insulated furnace.

Figure 2:
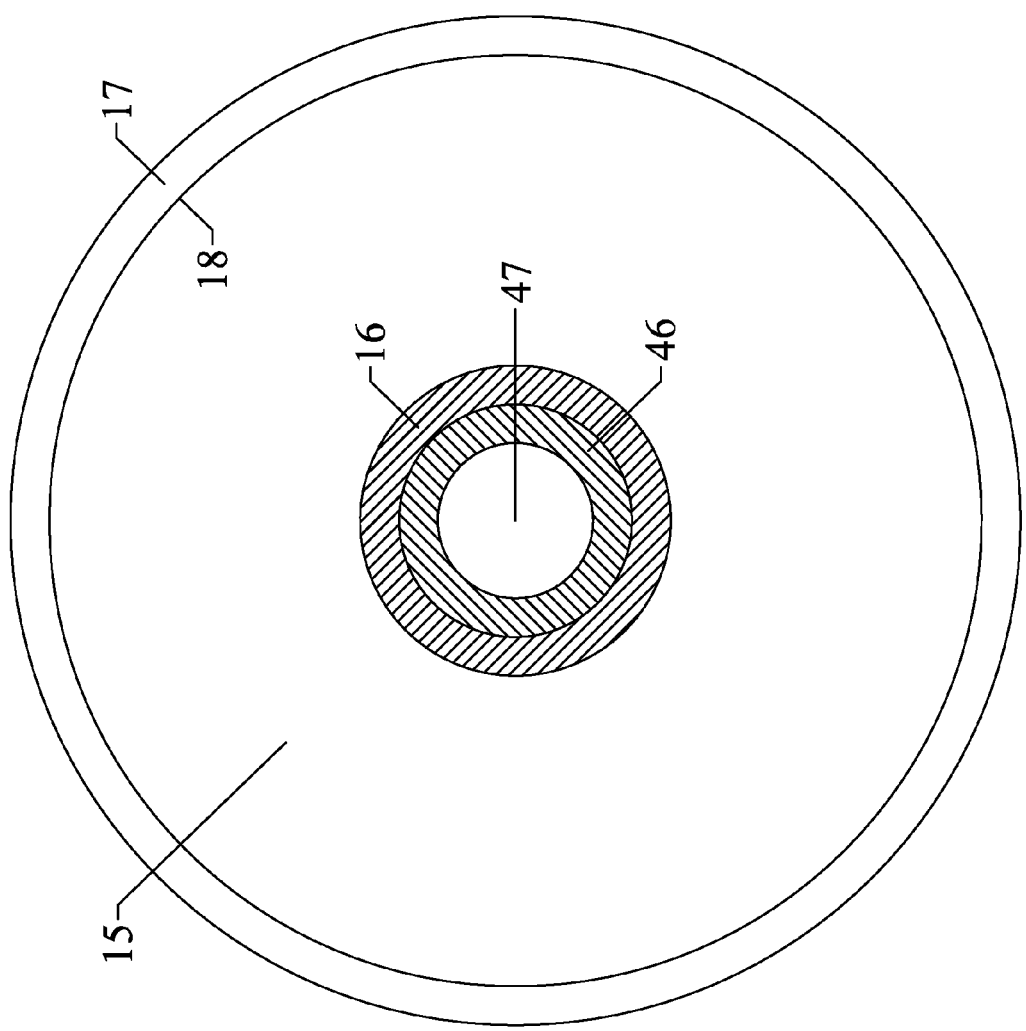
FIG. 2 is a top view of the entry ports of the insulated furnace.

FIG. 2 is a top view of the of the entry ports of the insulated furnace 28. The Figure further shows the tube 46 for receiving the blended air 47 through the first air intake 16. Second chamber 15 is depicted with the inner wall 17 outside the second air intake 18.

FIG. 3 shows a cross sectional view of the air gun 52 that can receive the pressurized air 44 through air inlet 58 and then into an air nozzle 54 that can be secured to the body 56 that can flow into the chamber 64.

An abrading media intake port 62 can allow the abrading media 48, 49 to enter the air gun via the meter 66, through the funnel 68, which can be located on pole 67, as shown in this Figure. The abrading media can then mix with the pressurized air 44 in the chamber 64 before flowing out through the tube 46 and becoming blended air 47. An air outlet 60 is also shown in the body 56 that can threadably engage the tube 46.

This Figure also shows the negative pressure gauge 74.

Figure 4:
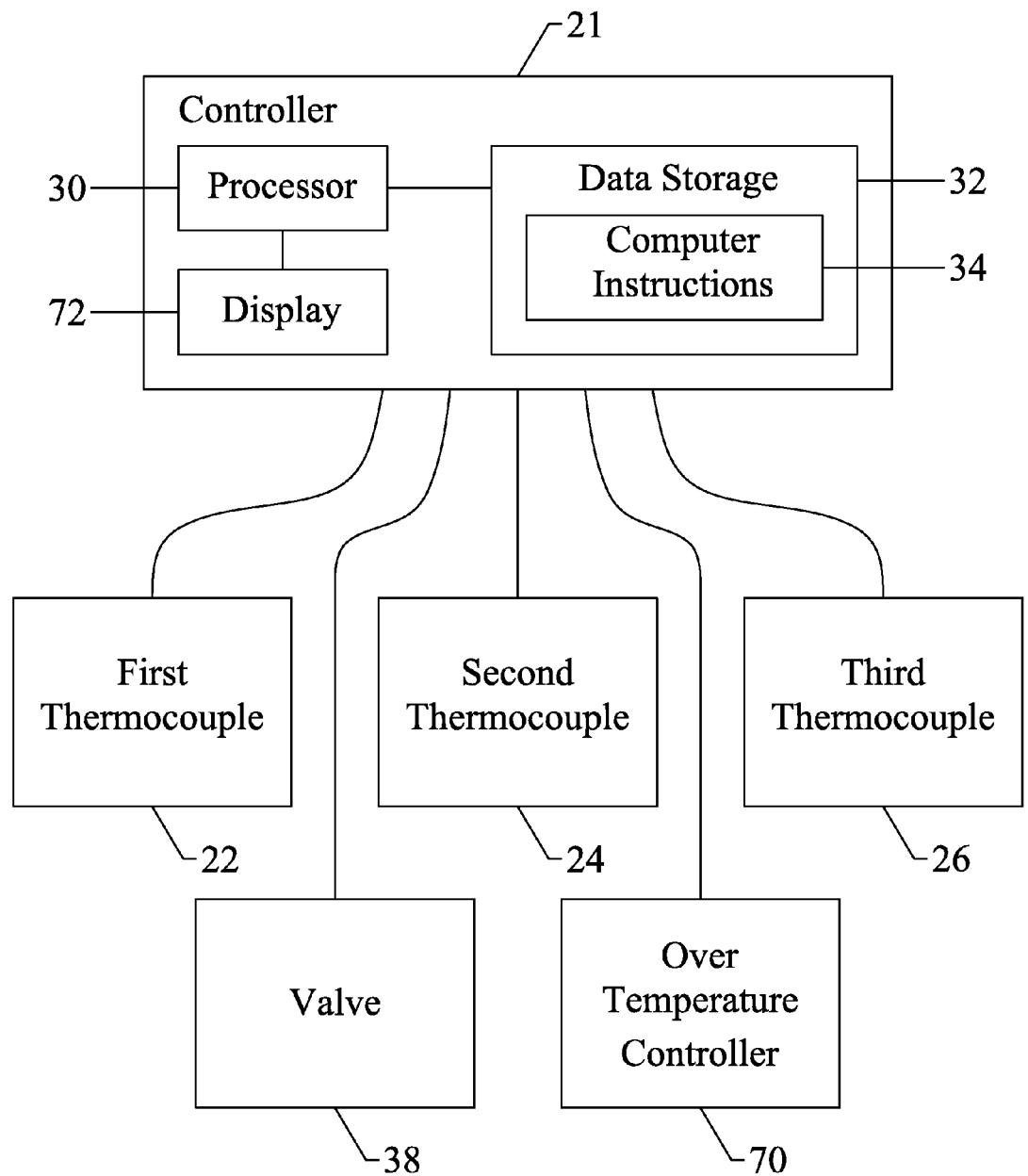
FIG. 4 is a diagram of the controller used in the system.

FIG. 4 shows the controller 21, which can have a processor 30 connected to data storage 32 and further having computer instructions 34 inside data storage. Also shown in this Figure, is display 72, which can be connected to the processor 30 for displaying information from one or more thermocouples. In this Figure, first thermocouple 22, second thermocouple 24 and third thermocouple 36 are shown connected to the controller. The valve 38 and over temperature controller 70 can further be connected to the controller.

In an embodiment, one or more thermocouples can be connected directly to the display. In additional embodiments, the one or more thermocouples can be connected wirelessly to the display.

The system can be a continuous process that can test from about 2 test specimens to about 20 test specimens sequentially.

In an embodiment, a first test specimen can be impacted by a first abrading media and a second test specimen can be impacted with a second abrading media. The first and second abrading medias can be of the same media or can be different medias.

The abrading media can be accelerated in velocity from the first air intake through the tube to the test specimen by at least about 20 percent from the initial velocity.

In an embodiment, the second chamber can have an inner wall that can extend at least 30 percent into the first chamber. The inner walls can be a tubular round or angular, such as octagonal.

While these embodiments have been described with emphasis on the embodiments, it should be understood that within the scope of the appended claims, the embodiments might be practiced other than as specifically described herein.

What is claimed is:

1. A system for testing abrasion resistance of at least one test specimen at elevated temperatures of at least 230 degrees Fahrenheit comprising:
    a. an insulated furnace comprising:
       (i) a housing forming a first chamber lined with a refractory material;
       (ii) an inner wall within the first chamber forming a second chamber, wherein the inner wall has a second air intake for flowing heated air at a temperature above the test temperature to the second chamber;
       (iii) a tube disposed within the second chamber;
       (iv) a first air intake within the inner wall for providing pressurized air at a temperature below a test temperature connected to the tube;
       (v) an exhaust port disposed through the housing in communication with the first chamber;
       (vi) a controller in communication with a first thermocouple adjacent the second air intake for monitoring heat air temperatures at the second air intake and in communication with a second thermocouple adjacent at the test specimen; and
       (vii) a closable opening in the housing for allowing the at least one test specimen to be placed in the first chamber;
    b. a burner for burning a fuel, in communication with a blower for forming heated air and for providing a variable flow of the heated air to the second air intake using a valve in communication with the controller;
    c. an air compressor for forming the pressurized air; and
    d. an air gun for receiving the pressurized air, blending the pressurized air with at least one abrading media and flowing the blended air to the tube disposed through the first air intake; wherein the blended air mixes with the heated air forming a mixed air at the test temperature for impacting with the test specimen.

2. The system of claim 1, wherein at least 2 test specimens to 20 test specimens are disposed in the first chamber for testing sequentially.

3. The system of claim 1, wherein a first test specimen is impacted by a first abrading media and a second test specimen is impacted by a second abrading media and the first and second abrading medias are different.

4. The system of claim 1, wherein each test specimen is mounted on a carrier.

5. The system of claim 1, wherein the at least one abrading media accelerates in velocity through the tube.

6. The system of claim 1, wherein the air gun comprises a meter connected to a pole, a funnel secured to the pole aligned with the meter, a body with a abrading media intake port for communicating from the funnel to a mixing chamber in the body, an air nozzle secured to the body for flowing the pressurized air into the mixing chamber, and an air outlet for flowing pressurized air mixed with abrading media out of the air gun.

7. The system of claim 1, wherein the inner walls are tubular and the inner walls extend at least 30 percent of the length of the first chamber into the first chamber.

8. The system of claim 1, further comprising a third thermocouple connected to the controller for measuring temperatures within the first chamber.

9. The system of claim 1, wherein the controller comprises a processor in communication with a data storage, a display in communication with the processor; computer instructions in data storage for instructing the processor to monitor temperature signals from the first and second thermocouples, compare the temperature signals to a predetermined limit in data storage and control the valve that restricts flow of fuel into the burner.

10. The system of claim 1, wherein the refractory material is either a ceramic, an insulating material capable of a low thermal conductivity or combinations thereof.

11. The system of claim 1, wherein the refractory material comprises at least two different refractory materials lining the first chamber.

12. The system of claim 1, wherein the test temperature is from 230 degrees Fahrenheit to 2000 degrees Fahrenheit.

13. The system of claim 1, wherein the refractory material lining the first chamber has a thickness ranging from 2 inches to 8 inches.

14. The system of claim 1, wherein the abrading media is a flowable particulate having a diameter from $\frac{1}{8}^{th}$ inch to 20 microns.

15. The system of claim 1, wherein the system is a one pass test system.

16. The system of claim 1, further comprising a pressurized air gauge for monitoring pressure of pressurized air from the air compressor and a regulator for controlling flow of pressurized air.

17. The system of claim 1, further comprising a negative pressure gauge for monitoring negative pressure of abrading media entering the air gun.

18. The system of claim 1, further comprising an over temperature controller connected to the controller for providing emergency shut off of the furnace when temperatures in the furnace exceed a predetermined limit.

19. The system of claim 1, further comprising an exhaust valve disposed over the exhaust port for regulating exhaust air from the insulated furnace.

* * * * *